United States Patent [19]
Wehr

[11] Patent Number: 5,520,628
[45] Date of Patent: May 28, 1996

[54] ANKLE ENCOMPASSING PRESSURE ORTHOSIS

[76] Inventor: Maxon P. Wehr, 135 S. Cochran, Charlotte, Mich. 48813

[21] Appl. No.: 229,211

[22] Filed: Apr. 18, 1994

[51] Int. Cl.$^6$ .................................... A61F 5/00
[52] U.S. Cl. ................ 602/27; 602/7; 602/23; 602/27; 602/65; 128/882
[58] Field of Search ............... 602/4, 5, 27, 16, 602/23, 65; 623/29, 47; 128/892, 888

[56] References Cited

U.S. PATENT DOCUMENTS

| | | |
|---|---|---|
| 101,743 | 4/1870 | King. |
| 143,537 | 10/1873 | Silberschmidt. |
| 1,129,525 | 2/1915 | Severy .................... 602/27 |
| 1,397,095 | 11/1921 | Hamilton. |
| 3,383,708 | 5/1968 | Pappas .................... 602/27 |
| 4,409,976 | 10/1983 | Pence. |
| 4,433,682 | 2/1984 | Badra. |
| 4,440,158 | 4/1984 | Shapiro .................... 602/27 |
| 4,489,719 | 12/1984 | Lapenskie .................... 602/27 |
| 4,587,962 | 5/1986 | Greene et al. ............... 128/80 |
| 4,776,326 | 10/1988 | Young et al. .................... 602/27 |
| 4,825,856 | 5/1989 | Nelson .................... 602/27 |
| 4,844,094 | 7/1989 | Grim. |
| 4,862,900 | 9/1989 | Hefele .................... 602/27 |
| 4,926,846 | 5/1990 | Nassar. |
| 4,955,149 | 9/1990 | Ottieri .................... 36/119 |
| 4,964,402 | 10/1990 | Grim et al. .................... 602/27 |
| 4,966,134 | 10/1990 | Bewer .................... 602/27 |
| 4,982,733 | 1/1991 | Broadhurst et al. .................... 602/27 |
| 5,090,404 | 2/1992 | Kallassy .................... 602/65 |
| 5,135,473 | 8/1992 | Epler et al.. |
| 5,152,400 | 10/1992 | Johnson, Jr. .................... 602/13 |
| 5,185,000 | 2/1993 | Brandt et al.. |
| 5,197,942 | 3/1993 | Brady .................... 602/5 |
| 5,213,564 | 5/1993 | Johnson, Jr. et al. .................... 602/27 |
| 5,242,379 | 9/1993 | Harris et al. .................... 602/27 |
| 5,330,419 | 7/1994 | Toronto et al. .................... 602/27 |

OTHER PUBLICATIONS

The Foot: Examination and Diagnosis Dr. Ian J. Alexander, pp. 8 and 9.

*Primary Examiner*—Richard J. Apley
*Assistant Examiner*—Kim M. Lee
*Attorney, Agent, or Firm*—Ian C. McLeod

[57] ABSTRACT

A custom fitted ankle brace (10) and a process for constructing the brace is described. The brace is comprised of anterior and posterior supports (12 and 16) connected together at their distal ends (12B and 16B) by pivot pins (22). The anterior and posterior supports both have arcuate sidewalls (12C and 16C) which form openings (14 and 18). When the brace is in the closed position around the ankle (102), the sidewall of the posterior support overlaps the sidewall of the anterior support and the opening of the anterior support is adjacent the achilles tendon of the ankle. The anterior support has a cushion (26) adjacent the inside surface (12H) to increase the user's comfort. To apply the brace, the proximal ends (12A and 16A) of the supports are pulled apart and the user (100) inserts his foot (104) into the brace and pulls the brace into position around his ankle. The brace is then secured on the ankle by a securing strap (28) extending around the proximal end of the supports. To construct the brace, supports are fabricated according to the user's measurements, preferably using patterns (34 and 36). The supports are then heated and formed onto a cast (32) of the user's ankle and foot. The anterior support is formed first and the posterior support is formed over the anterior support. The supports are then removed from the cast and connected together.

37 Claims, 4 Drawing Sheets

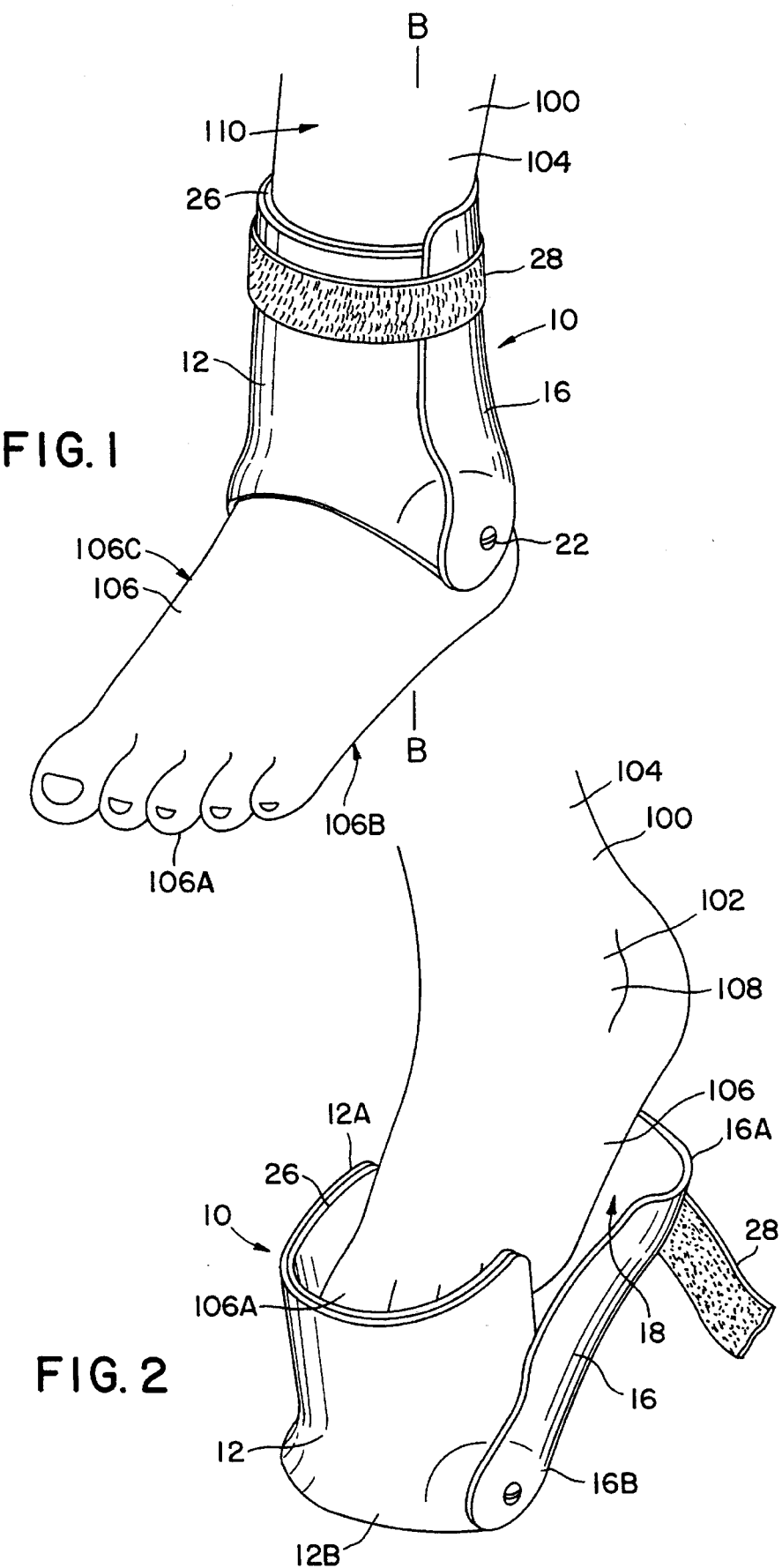

ANKLE ENCOMPASSING PRESSURE ORTHOSIS

BACKGROUND OF THE INVENTION

1. Field of the Invention

The present invention relates to a brace which provides encompassing pressure around the ankle to limit eversion and inversion of the ankle and the foot. In particular, the present invention relates to a custom fitted brace which extends over the ankle and provides encompassing pressure around the subtalar joint and the ankle joint to limit inversion and eversion of the ankle and the foot.

The subtalar joint consists of the articulation of the inferior surface of the talus and the superior surface of the calcaneus. The subtalar joint is a gliding joint permitting limited motion in all directions. The basic motions are inversion and eversion. Inversion is turning of the foot such that the medial side (inside) of the foot is upward. Eversion is turning of the foot such that the lateral side (outside) of the foot is upward. Inversion and eversion is shown in FIG. 5 of *The Foot: Examination and Diagnosis,* Dr. Ian J. Alexander, Page 9. The ankle joint is formed by the inferior ends of the tibia and the fibula and the superior surface of the talus. The ankle joint is a hinged joint allowing dorsiflexion and plantar flexion. Dorsiflexion is bending the foot backward or upward. Plantar flexion is bending the foot downward. Dorsiflexion and plantar flexion is shown in FIG. 4 of *The Foot: Examination and Diagnosis,* Dr. Ian J. Alexander, Page 8. To limit inversion and eversion of the ankle and the foot, movement of the subtalar must be limited. However, to allow the patient to be ambulatory, dorsiflexion and plantar flexion of the foot must not be substantially affected.

2. Prior Art

Definitions for all the relevant medical terms can be found in *Dorland's Medical Dictionary Shorter Edition,* (Saunders Company, 1980). In addition, specific information relating to the ankle and the foot can be found in *The Foot: Examination and Diagnosis,* Ian J. Alexander, (Churchill Livingstone Inc., 1990).

The prior art has described various types of ankle braces and supports. Illustrative are U.S. Pat. Nos. 101,743 to King; 143,537 to Silberschmidt; 1,397,095 to Hamilton; 4,409,976 to Pence; 4,433,682 to Badra; 4,844,094 to Grim; 5,135,473 to Epler et al; and 5,185,000 to Brandt et al.

In particular, U.S. Pat. No. 4,926,846 to Nassar describes an ankle wrap for limiting the intermalleolar expansion in the ankle during physical activity. The wrap consists of two separate straps which are wrapped around the ankle to provide compressive pressure to the mortise. The straps are wrapped completely around the ankle and are secured end to start by a hook and loop closure.

None of the prior art patents show an ankle brace which is easily and quickly applied to the ankle and which provides the necessary pressure to limit the inversion and eversion of the ankle and foot and which also supports the ankle without being bulky or uncomfortable to wear. Thus, there remains a need for an ankle brace which is custom fitted to the user to provide encompassing pressure around the ankle to limit inversion and eversion of the ankle and the foot while allowing dorsiflexion and plantar flexion of the ankle and the foot to allow the user to remain ambulatory.

OBJECTS

It is therefore an object of the present invention to provide a custom fitted brace which provides encompassing pressure to the ankle. Further, it is an object of the present invention to provide a custom fitted brace which limits inversion and eversion of the ankle and foot while allowing unhindered dorsiflexion and plantar flexion of the ankle and foot. Still further, it is an object of the present invention to provide an ankle brace which is inconspicuous and easily hidden. Furthermore, it is an object of the present invention to provide an ankle brace which is easily applied and removed from the ankle. Finally, it is an object of the present invention to provide a custom fitted ankle brace which is lightweight, durable and easy to construct.

BRIEF DESCRIPTION OF THE DRAWINGS

FIG. 1 is a perspective view of the custom fitted ankle brace 10 in the closed position mounted around the ankle 102 of the user 100.

FIG. 2 is a perspective view of the custom fitted ankle brace 10 of FIG. 1 showing the brace 10 in the open position with the foot 104 of the user 100 entering the brace 10 with the toes 106A first.

DETAILED DESCRIPTION OF THE PREFERRED EMBODIMENTS

Figure 3:
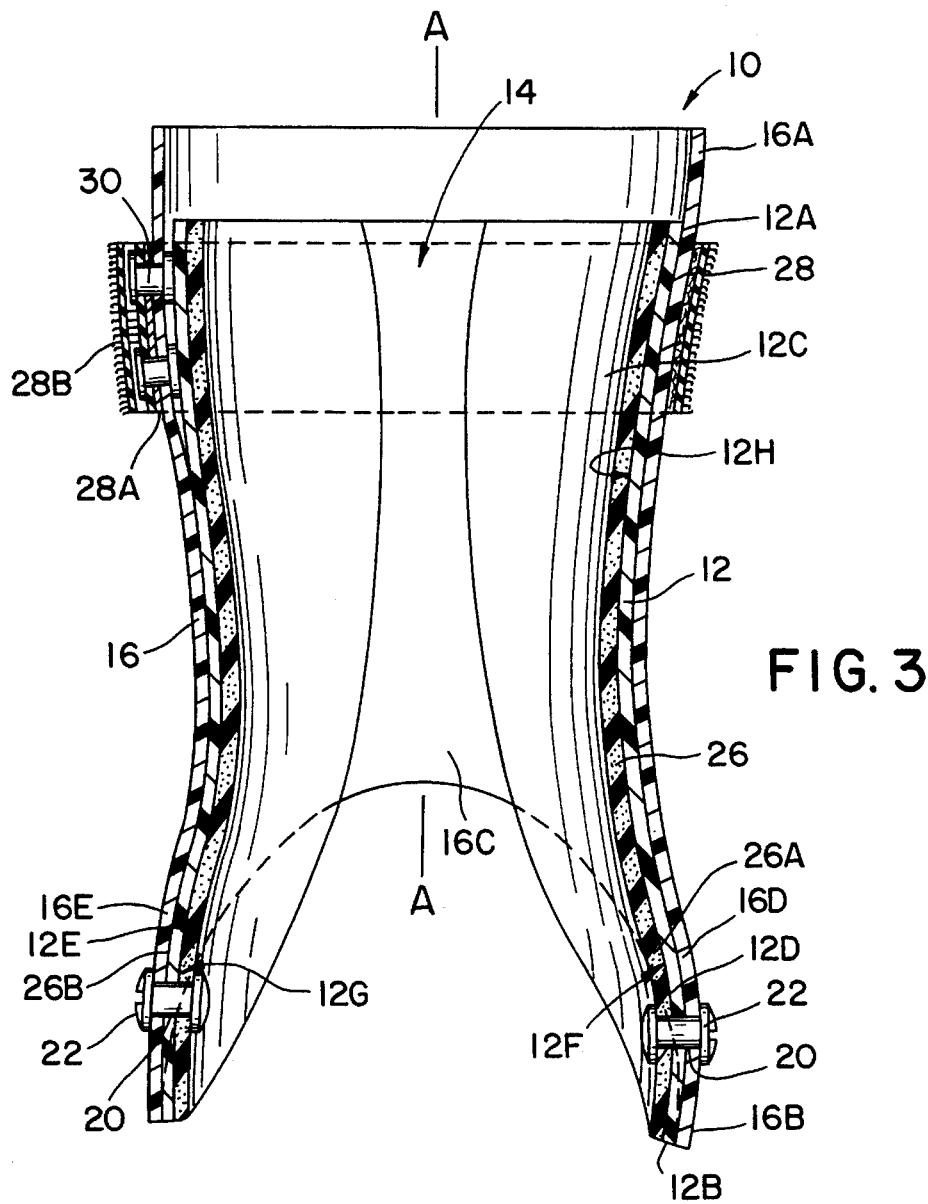
FIG. 3 is a cross-sectional view of the custom fitted ankle brace 10 of FIG. 1 showing the tabs 16D and 16E of the posterior support 16 overlapping the tabs 12D and 12E of the anterior support 12 with the pivot pin 22 extending through the tabs 12D and 16D and 12E and 16E and the cushion 26.

The present invention relates to a custom fitted brace for limiting eversion and inversion of an ankle and a foot, which comprises: an anterior support means to be mounted adjacent to and conform to an anterior portion of the ankle; a posterior support means pivotably connected to the anterior support means and to be mounted adjacent to and conform to a posterior portion of the ankle, wherein the anterior support means and the posterior support means together provide encompassing pressure around the circumference of the ankle and the foot.

Further, The present invention relates to a custom fitted brace for limiting eversion and inversion of an ankle and a foot which comprises: an anterior support means having a proximal end and a distal end with an arcuate sidewall therebetween to be mounted adjacent to and conform to an anterior portion of the ankle with the distal end of the anterior support means adjacent the foot; and a posterior support means having a proximal end and a distal end with an arcuate sidewall therebetween pivotably connected to the anterior support means to be mounted adjacent to and conform to a posterior portion of the ankle with the distal end of the posterior support means adjacent the foot, wherein the anterior support means and the posterior support means together provide encompassing pressure around the ankle and the foot.

Furthermore, the present invention relates to a custom fitted brace for limiting eversion and inversion of an ankle and a foot which are attached to a leg, which comprises: an anterior support means to be mounted adjacent to and conform to an anterior portion of the ankle, the anterior support means having an arcuate sidewall between a proximal open end and a distal open end along and around a longitudinal axis of the leg; and a posterior support means pivotably connected to the anterior support means to be mounted adjacent to and conform to a posterior portion of the ankle, the posterior support means having an arcuate sidewall between a proximal open end and a distal open end along and around the longitudinal axis of the leg, wherein the sidewalls define an opening extending between the distal open ends and the proximal open ends and wherein when mounted around the ankle, the anterior support means and the posterior support means together provide encompassing pressure around the circumference of the ankle and the foot.

Still further, the present invention relates to a method for limiting inversion and eversion of an ankle and a foot, which comprises: providing a custom fitted brace for limiting eversion and inversion of an ankle and a foot which comprises: an anterior support means having a proximal end and a distal end with an arcuate sidewall therebetween to be mounted adjacent to and conform to an anterior portion of the ankle with the distal end of the anterior support means adjacent the foot; and a posterior support means having a proximal end and a distal end with an arcuate sidewall therebetween pivotably connected to the anterior support means to be mounted adjacent to and conform to a posterior portion of the ankle with the distal end of the posterior support means adjacent the foot, wherein the anterior support means and the posterior support means together provide encompassing pressure around the ankle and the foot; moving the anterior support means and the posterior support means of the brace apart; inserting the foot into the brace adjacent the proximal end of the anterior support means and the proximal end of the posterior support means; positioning the brace over the ankle such that the anterior support means is adjacent the anterior portion of the ankle and the posterior support means is adjacent the posterior portion of the ankle; pivoting the anterior support means and the posterior support means together such as to encompass the ankle; and securing the brace around the ankle such that the brace exerts encompassing pressure around the circumference of the ankle and the foot and limits inversion and eversion of the ankle and the foot.

Finally, the present invention relates to a process for custom fitting a brace for limiting eversion and inversion of an ankle and a foot which comprises the steps of: creating a positive cast means of the ankle and the foot; measuring the circumference of the ankle and the foot including the malleolus bones of the ankle; fabricating an anterior support means having an essentially rectangular shape with two short sides and two long sides and a posterior support means having a polygonal shape with a short side, two longer angled sides adjacent the short side and a side opposite the short side; heating the anterior support means and forming the anterior support means on the positive cast means; removing the anterior support means from the positive cast means; trimming the anterior support means in order to comfortably accommodate the ankle and the foot; placing the anterior support means back on the positive cast means; heating the posterior support means and forming the posterior support means on the positive cast means; removing the anterior support means and the posterior support means from the positive cast means; trimming the posterior support means in order to comfortably accommodate the ankle and the foot; and pivotably connecting the anterior support means and the posterior support means together.

The custom fitted brace provides 360° pressure around the circumference of the ankle and the foot and particularly around the subtalar joint of the ankle. The custom fitted brace is secured onto the ankle by a strap means. The anterior and posterior supports are pivotally connected together preferably by a quick-release rivet.

Figure 7:
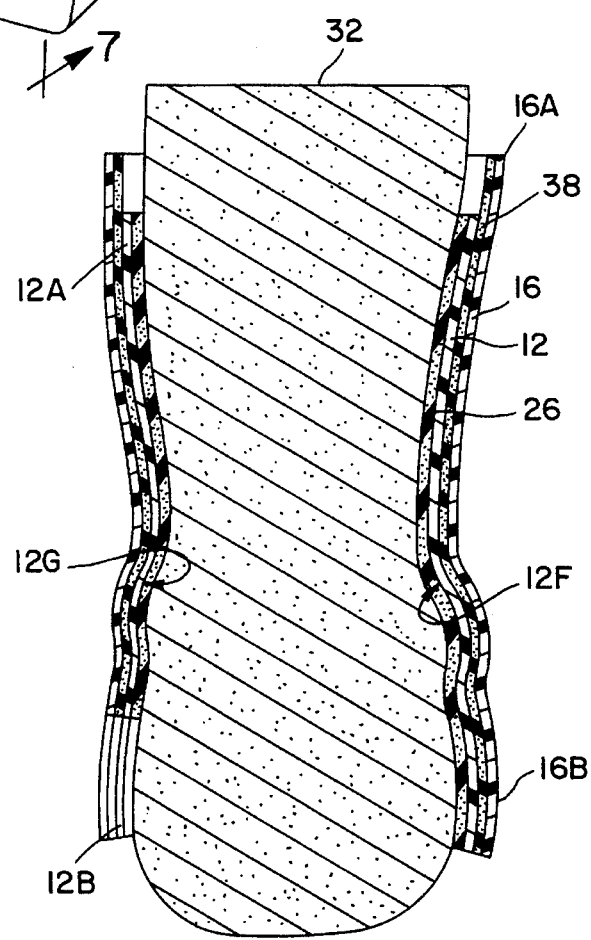
FIG. 7 is a cross-sectional view of FIG. 6 along the line 7—7 showing the cushion 26, the posterior support 16, the parting agent 38 and the anterior support 12 all mounted on the positive cast 32.

FIGS. 1 to 3 show the custom fitted ankle brace 10 or orthosis of the current invention. The brace 10 has an anterior support 12 and a posterior support 16 pivotably connected together by pivot pins 22. The anterior support 12 has a proximal end 12A and a distal end 12B with an arcuate sidewall 12C therebetween. The arcuate sidewall 12C provides an opening 14 parallel to the axis A—A of the brace 10, when the brace 10 is in the fully closed position (FIG. 3). When in the fully closed position on the ankle 102, the axis A—A of the brace 10 is preferably aligned with the longitudinal axis B—B of the lower leg 104 of the user 100 (FIG. 1). The distal end 12B of the anterior support 12 has opposed first and second tabs 12D and 12E adjacent the opening 14. The tabs 12D and 12E extend outward from the distal end 12B of the brace 10 parallel to the axis A—A. In the preferred embodiment, the tab 12D and 12E have a semi-circular shape and do not extend beyond the arcuate sidewall 12C into the opening 14. The sidewall 12C of the anterior support 12 adjacent the first tab 12D preferably has a first convex portion 12F which extends over and accommodates the lateral malleolus 108 of the user 100 (FIGS. 1 and 7). In addition, a second convex portion 12G adjacent the second tab 12E may also be needed to accommodate the medial malleolus (not shown), depending on the particular shape of the ankle 102 of the user 100 since the brace 10 is custom fitted to closely follow the particular shape of a user's ankle 102. The exact shape of the sidewall 12C of the anterior portion 32A depends on the shape of the user's ankle 102.

The posterior support 16 is similar in shape to the anterior support 12. The posterior support 16 has a proximal end 16A and a distal end 16B with an arcuate sidewall 16C therebetween. The arcuate sidewall 16C provides an opening 18 extending parallel to the axis A—A of the brace 10 when the brace 10 is in the fully closed position (FIG. 2). The distal end 16B of the posterior support 16 has opposed first and second tabs 16D and 16E adjacent the opening 18 which extend outward from the distal end 16B parallel to the axis A—A. The tabs 16D and 16E preferably have a shape and size similar to the shape and size of the tabs 12D and 12E of the anterior support 12 (FIG. 1).

The exact size of the supports 12 and 16 is necessarily dependent on the size of the ankle 102, leg 104 and foot 106 of the user 100. In general, however, the inner diameter of the arcuate sidewall 16C of the posterior support 16 is slightly greater than the outer diameter of the arcuate sidewall 12C of the anterior support 12 such that the sidewall 16C of the posterior support 16 is able to overlap the sidewall 12C of the anterior support 12 (FIG. 3). The opening 18 of the posterior support 16 is also wider than the outer diameter of the sidewall 12C of the anterior support 12 in order to allow the anterior support 12 to fit within the opening 18 of the posterior support 16 such that the sidewall 16C of the posterior support 16 overlaps the sidewall 12C of the anterior support 12 when the brace 10 is in the closed position. Preferably, the width of the opening 18 of the posterior support 16 and the width of the inner diameter of the arcuate sidewall 16C of the posterior support 16 are identical. The different circumferences of the arcuate sidewalls 12C and 16C of the supports 12 and 16 also enables the tabs 12D and 16D and 12E and 16E of the supports 12 and 16 to be aligned and to overlap in order to be able to be pivotably connected together. In particular, the arcuate sidewall 12C of the anterior support 12 forms almost a complete circle leaving only about a 1 to 2 inch (2.54 to 30.48 cm) opening 14 (FIG. 3). The arcuate sidewall 16C of the posterior support 16 has a small circumference and essentially only forms a semicircle. Thus, the anterior support 12 extends around almost the entire ankle 102 while the posterior support 16 extends around only about one half of the ankle 102 (FIG. 1). The sidewall 16C of the posterior support 16 is preferably taller than the sidewall 12C of the anterior support 12 such that the proximal end 16A of the posterior support 16 extends upward beyond the proximal end 12A of the anterior support 12. Preferably, the anterior support 12 is approximately six (6) inches (15.24 cm) high and the posterior support 16 is approximately seven (7) inches (17.78 cm) high. The exact height of the supports 12 and 16 is necessarily determined by the size of the ankle 102 of the particular user 100 and also the amount of the user's leg 104 that is to be covered. The height of the supports 12 and 16 can be adjusted to increase the comfort of the user 100. The size of the supports 12 and 16 are selected to maximize the comfort of the user 100. In the preferred embodiment, the supports 12 and 16 are constructed from a very firm thermoplastic material such as a high temperature subortholene which is lightweight and durable and easily formable when heated. Both of the supports 12 and 16 are preferably identical in thickness and are 1/16 to 1/4 inch (0.16 to 0.64 cm) thick (FIG. 3).

Figure 3A:
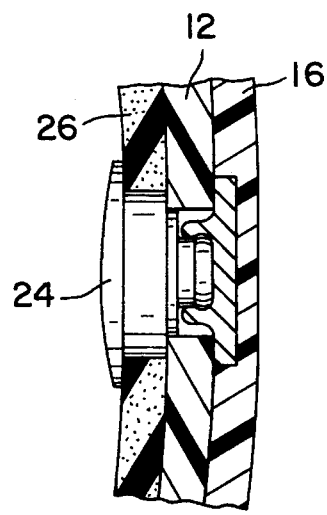
FIG. 3A is a cross-sectional view of the custom fitted ankle brace 10 of FIG. 1 showing the quick release rivet 24.

The pivot pins 22 connect the distal ends 12B and 16B of the anterior and posterior supports 12 and 16 together. The pivot pins 22 extend through holes 20 in the tabs 12D, 12E, 16D and 16E of the supports 12 and 16 to connect the first tab 12D of the anterior support 12 to the first tab 16D of the posterior support 16 and similarly connect the second tabs 12E and 16E of the supports 12 and 16 together. Preferably, the holes 20 are of the same size and are positioned in the tabs 12D, 12E, 16D and 16E such that the tabs 12D and 12E of the anterior support 12 match the tabs 16D and 16E of the posterior support 16, respectively, when the holes 20 are aligned. The pivot pins 22 are preferably circular with a diameter slightly smaller than the holes 20 in the supports 12 and 16. This enables the proximal ends 12A and 16A of the supports 12 and 16 to be pivoted apart in order to enable a user 100 to insert his foot 106 into the brace 10 in order to position the brace 10 around his ankle 102. In an alternate embodiment, quick-release rivets 24 are used to connect the supports 12 and 16 together (FIG. 3A). The quick-release rivets 24 are easily removed from the brace 10 to enable the supports 12 and 16 to be easily disconnected from each another. The quick-release rivets 24 allow the user 100 to position the supports 12 and 16 around his ankle 102 and then insert the quick-release rivets 24 to connect the supports 12 and 16 together. The quick-release rivets 24 eliminate the need for the user 100 to pivot the proximal ends 12A and 16A of supports 12 and 16 apart in order to insert the foot 106 to position the brace 10 on the ankle 102. This is especially important for users 100, such as the elderly or handicapped, who have limited movement in their feet or who have trouble moving or bending in general.

A cushion 26 is preferably provided on the inside surface 12H of the anterior support 12. The cushion 26 is preferably identical in shape and size to the anterior support 12. The cushion 26 has first and second tabs 26A and 26B which are provided adjacent the first and second tabs 12D and 12E of the anterior support 12 (FIG. 3). The cushion 26 is preferably adjacent the users skin 110 when the brace 10 is positioned around the ankle 102. The cushion 26 provides additional comfort for the user 100 while wearing the brace 10. The cushion 26 is preferably constructed from a polyethylene open cell foam such as Plastazote™, manufactured by Zotefoams Limited, located in the United Kingdom and is preferably about 1/4 to 3/8 inch (0.64 to 0.95 cm) thick.

A securing strap 28 is provided around the brace 10 to secure the brace 10 tightly around the ankle 102 (FIG. 1). Preferably, the strap 28 is attached at the first end 28A to the proximal end 16A of the posterior support 16. The strap 28 is then wrapped around the proximal end 12A of the anterior support 12 and the proximal end 16A of the posterior support 16 such that the second end 28B of the securing strap 28 overlaps the first end 28A in order that the brace 10 is completely encircled by the strap 28 (FIG. 3). The strap 28 is preferably a two-sided hook and loop fabric fastener. The strap 28 is preferably 1½ inches (3.81 cm) wide and at least of a length such as to completely surround the brace 10 to allow sufficient overlap of the ends 28A and 28B of the strap 28 to provide adequate holding power. The strap 28 is preferably mounted onto the proximal end 16A of the posterior support 16 by rivets 30. Alternately, the strap 28 could be independent of the brace 10 and be secured onto the brace by a loop ring (not shown). It is understood that a variety of types of securing devices could be used to ensure that the ankle brace 10 remains in place securely around the ankle 102 such as to provide encompassing pressure at all times.

Figure 4:
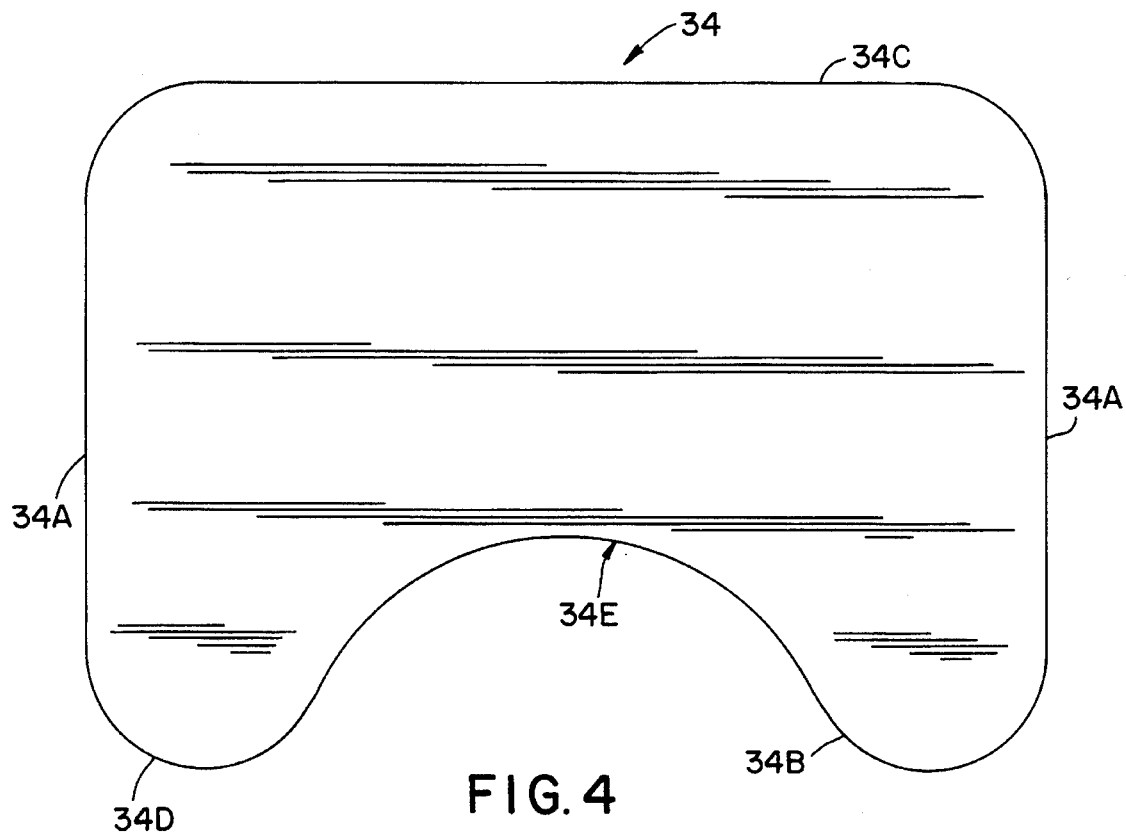
FIG. 4 is a front view of the anterior pattern 34 showing the rounded corners 34D and the semicircular indentation 34E cut out of one of the long sides 34B.
Figure 5:
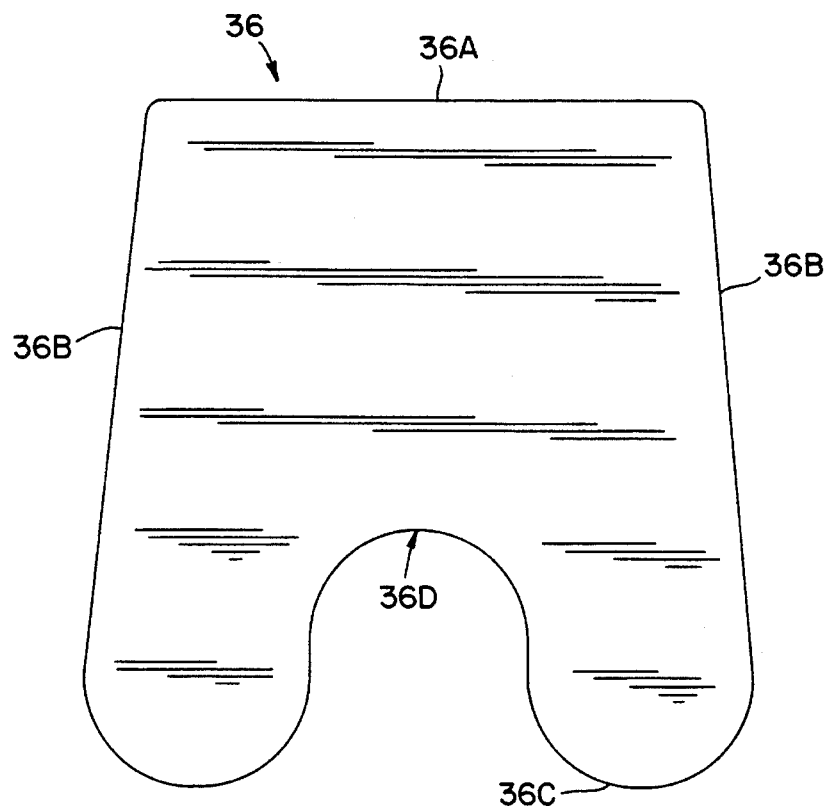
FIG. 5 is a front view of the posterior pattern 36 showing the short sides 36A, the two long sides 36B and the semicircular indentation 36D in the side 36C opposite the short side 36A.
Figure 6:
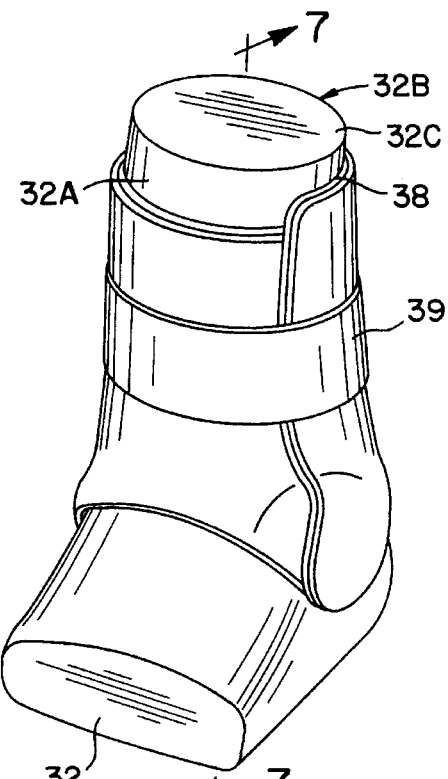
FIG. 6 is a front perspective view of the posterior support 16 and the anterior support 12 formed on the positive cast 32.

To construct the brace 10, the user's foot 106, ankle 102 and lower leg 104 are first measured. A positive cast 32 of the user's foot 106, ankle 102 and lower leg 104 is created using the user's measurements (FIG. 6). The cast 32 is preferably made of plaster and is similar to those already known. Next, an anterior pattern 34 and a posterior pattern 36 are constructed using additional user measurements (FIGS. 4 and 5). The patterns 34 and 36 are preferably constructed from corrugated cardboard although, a variety of materials can be used.

To determine the measurement for the anterior pattern 34, the ankle 102 is measured starting at the achilles tendon (not shown) and proceeding medially over the medial malleolus over the instep 106C to the lateral malleolus 108 and back to the achilles tendon. This measurement provides the length of the long sides 34B and 34C of the anterior pattern 34 which is the circumference of the anterior support 12. As shown in FIG. 4, the anterior pattern 34 is generally rectangularly shaped having two short sides 34A and two long sides 34B and 34C with rounded corners 34D. The height of the short sides 34A of the anterior pattern 34 is essentially the same for each user 100 and is preferably approximately six (6) inches (15.24 cm). However, the height of the short sides 34A will depend upon the amount of the leg 104 of the user 100 that is to be covered. A semicircular indentation 34E is cut out of one of the long sides 34B of the pattern 34 in order to provide for the tabs 12D and 12E of the anterior support 12 and also the tabs 26A and 26B of the cushion 26. The semicircular indentation 34E is preferably located at the center of the long side 34B.

As shown in FIG. 5, the posterior pattern 36 has a short side 36A with two angled sides 36B extending outward from the short side 36A and angling away from each other. Preferably, the two angled sides 36B are identical in length. A fourth side 36C, opposite the short side 36A extends between the two long sides 36B and has a semicircular indentation 36D located at the center. The semicircular indentation 36D provides for the tabs 16D and 16E of the posterior support 16. The height of the two angled sides 36B is preferably identical for each user and is approximately seven (7) inches (17.8 cm). The exact size and shape of the anterior pattern 34 and the posterior pattern 36 depends upon the measurements of the user 100.

Once the patterns 34 and 36 have been created, the supports 12 and 16 and cushion 26 are fabricated. The cushion 26 is cut first using the anterior pattern 34. The cushion 26 is then heated in a convection oven (not shown) at 250° and formed onto the anterior position 32A of the positive cast 32. The material is either vacuum formed or hand formed over the cast 32. The symmetry of the cushion 26 allows the cushion 26 to be mounted with either side adjacent the cast 32 provided the tabs 26A and 26B extend downward on either side towards the foot 104. The cushion 26 is formed on the cast 32 such that the tabs 26A and 26B of the cushion 26 extend downward beyond the lateral and medial malleolus 108 of the ankle 102. The cushion 26 is first formed on the anterior portion 32A of the cast 32 such that the tabs 26A and 26B on either side pointing towards the plantar surface of the foot 106. The cushion 26 is then formed laterally and medially, encompassing the cast 32 towards the achilles tendon. When correctly formed on the cast 32, the tabs 26A and 26B of the cushion 26 are approximately one (1) inch (2.54 cm) above the sole 106B of the foot 106 (FIG. 7). The cushion 26 is formed on the positive cast 32 such that only the extreme posterior portion 32B of the cast 32 which represents the achilles tendon is uncovered. Preferably, only approximately 1 inch of the extreme posterior portion 32B of the cast 32 is left uncovered. Next, the anterior support 12 is cut from a sheet of very firm thermoplastic material using the anterior pattern 34. The anterior support 12 is then heated in a preheated convection oven at 350° and formed onto the positive cast 32, similarly to the forming of the cushion 26 onto the cast 32. Preferably, the anterior support 12 is positioned directly over the cushion 26. Thus, the anterior support 12 also extends over the lateral and medial malleolus 108 and leaves the extreme posterior portion 32B of the cast 32 uncovered.

Once the cushion 26 and the anterior support 12 have cooled, the cushion 26 and anterior support 12 are removed from the cast 32. The placing of the heated anterior support 12 over the cushion 26 adheres the cushion 26 to the anterior support 12, eliminating the need for an adhesive or any other fastening means. The support 12 and cushion 26 are then trimmed of excess material in order to provide a better fit for maximum comfort for the user 100. Trimming the cushion 26 and support 12 is necessary because of the stretching of the materials during forming.

The anterior support 12 with the cushion 26 attached is then replaced on the cast 32. Next, a parting agent 38 is formed using the posterior pattern 36 such that it is approximately the same size and shape as the posterior support 16. The size and shape of the parting agent 38 need not be exact as long as it is at least the size of the posterior support 16. Preferably, the parting agent 38 is constructed from the same material as the cushion 26. The parting agent 38 is formed onto the posterior portion 32C of the cast 32. The parting agent 38 is preferably cold formed on the cast 32. The parting agent 38 may be heated however to ease forming. The parting agent 38 is formed onto the cast 32 such that the extreme posterior portion 32B of the cast 32 and the anterior support 12, including the tabs 12D and 12E, is covered by the parting agent 38.

Next, the posterior support 16 is cut from the same material as the anterior support 12 using the posterior pattern 36. The posterior support 16 is then heated and formed onto the positive cast 32 over the parting agent 38 (FIG. 7). An anti-stick substance (not shown) such as a powder is preferably placed between the parting agent 38 and the posterior support 16 to prevent the parting agent 38 from adhering to the posterior support 16 during forming. Preferably, the posterior support 16 is smaller in size and shape than the parting agent 38 and extends over only the portion of the anterior support 12 protected by the parting agent 38. The posterior support 16 is formed on the cast 32 such that the tabs 16D and 16E of the posterior support 16 are aligned with the tabs 12D and 12E of the anterior support 12. Once the posterior support 16 is correctly positioned, a securing tape 39 is wrapped around the supports 12 and 16 (FIG. 6). Preferably, the securing tape 39 is a tape which will adhere to the heated posterior support 16 and is easy to remove once the posterior support 16 has cooled. The posterior support 16 and parting agent 38 are then allowed to cool (FIG. 6).

Once the posterior support 16 and the parting agent 38, if necessary, have cooled the securing tape 39 is removed and the posterior support 16, the parting agent 38, the cushion 26 and the anterior support 12 are removed from the cast 32. The cast 32, parting agent 38 and securing tape 39 are discarded. The parting agent 38 is merely used to prevent the posterior support 16 from adhering to the anterior support 12 during forming of the brace 10. Next, the posterior support 16 is aligned with the anterior support 12 and is trimmed of excess material in order to provide maximum comfort for the user 100. The brace 10 is then polished to remove any rough edges and to improve the aesthetic quality of the brace 10. Holes 20 are drilled or punched in the distal ends 12B and 16B of the supports 12 and 16 through each of the tabs 12D, 12E, 26A and 26B of the anterior support 12 and the cushion 26 and the tabs 16D and 16E of the posterior support 16. The pivot pins 22 or the quick-release rivets 24 are placed through the holes 20 to pivotably connect the distal ends 12B and 16B of the supports 12 and 16 together. The securing strap 28 is then riveted to the proximal end 16A of the posterior support 16 and the brace 10 is ready for use.

IN USE

The proximal ends 12A and 16A of the supports 12 and 16 are pulled apart, pivoting around the pivot pins 22 at the distal ends 12B and 16B of the supports 12 and 16. Preferably, the supports 12 and 16 are able to be pivoted up to about 180° apart to allow the user 100 to insert his foot 106 into the brace 10. Once the brace 10 is in the open position, the user 100 slips his foot 106, toes 106A first, into the opening formed at the proximal ends 12A and 16A of the supports 12 and 16 (FIG. 2). The user 100 inserts his foot 106 into the brace 10 such that the anterior support 12 is adjacent the anterior portion 32A of the ankle 102. The user 100 then pulls the brace 10 upward to correctly locate the brace 10 around the ankle 102. The anterior support 12 is positioned on the ankle 102 such that the tabs 12D and 12E extend beyond the malleoli 108 (one shown) of the ankle 102 towards the user's foot 106 and the opening 14 of the anterior support 12 is adjacent the extreme achilles tendon of the ankle 102. Preferably, the distal end 12B of the anterior support 12 between the tabs 12D and 12E is spaced slightly above the top of the foot 106. The lateral malleolus 108 should be positioned within the first convex portion 12F of the anterior support 12. The user 100 should be able to tell when the brace 10 is positioned correctly due to the comfort of the custom fit. Next, the user 100 pivots the supports 12 and 16 towards each other to bring the brace 10 into the closed position around the ankle 102 (FIG. 1).

In an alternate embodiment, the quick-release rivet 24 enables the supports 12 and 16 to be completely detached from one another (FIG. 3A). In this embodiment, the user 100 releases and removes the rivets 24 and takes the brace 10 apart. Next, he places the anterior support 12 around the anterior portion 32A of the ankle 102. While holding the anterior support 12 in place, the user 100 positions the posterior support 16 over the back of the ankle 102 and over the opening 14 of the anterior support 12 such that the posterior support 16 extends over the sidewall 12C of the anterior support 12. The posterior support 16 is positioned such that the tabs 16D and 16E of the posterior support 16 are adjacent the tabs 12D and 12E, respectively, of the anterior support 12 and the holes 20 of the anterior support 12 are aligned with the holes 20 of the posterior support 16. Next, the user 100 inserts the quick-release rivets 24 into the holes 20 of the tabs 12D, 12E, 16D and 16E on either side of the brace 10.

Finally, with either embodiment, the user 100 secures the strap 28 around the brace 10 to firmly hold the brace 10 in place on the ankle 102. The brace 10 now provides 360° of encompassing pressure around the ankle 102. In particular, the brace 10 provides encompassing pressure around the subtalar joint and the ankle joint of the ankle 102. This pressure limits the inversion and eversion of the subtalar joint while continuing to allow the user 100 to be ambulatory. The brace 10 is ideal for persons having osteoarthritis (a degenerative joint disease) and will relieve the pain associated with arthrosis and arthrodesis while enabling the user 100 to be ambulatory. The brace 10 is also used to restrict the ankle joint to promote healing such as with torn ligaments, ankle sprains or fractures of the ankle joints. The brace 10 is preferably positioned around a bare ankle, although, the brace 10 can also be used over a sock or some other type of thin material. Preferably, the brace 10 is of such a size as to be easily hidden beneath the hem of slacks or pants and does not interfere with the normal use of shoes or pants. The brace 10 may also be provided in any color or with designs as needed to increase the aesthetic quality of the brace 10.

Numerous variations will occur to those skilled in the art. It is intended that the foregoing description be only illustrative of the present invention and that the present invention be only limited by the hereinafter appended claims.

I claim:

1. A custom fitted brace for limiting eversion and inversion of an ankle and a foot and allowing dorsiflexion and plantar flexion of the ankle and the foot, which comprises:
   a firm anterior support means to be mounted adjacent to and conform to an anterior portion of the ankle, wherein the anterior support means extends only slightly outward away from the ankle over the top of the foot so as to allow dorsiflexion of the foot;
   a firm posterior support means connected by a quick-release rivet to the anterior support means and to be mounted adjacent to and conform to a posterior portion of the ankle, wherein the anterior support means and the posterior support means together extend downward beyond the malleoli of the ankle and provide encompassing pressure around the circumference of the ankle and the foot.

2. The brace of claim 1 wherein the brace provides 360° pressure around the circumference of the ankle and the foot.

3. The brace of claim 1 wherein the brace provides an encompassing pressure around and on the subtalar joint of the ankle to minimize inversion and eversion of the subtalar joint.

4. The brace of claim 1 wherein a cushion means is provided between the anterior portion of the ankle and the anterior support means.

5. The brace of claim 4 wherein the cushion means is constructed of a thermo polyethylene open cell foam.

6. The brace of claim 1 wherein the anterior support means and the posterior support means are constructed of a thermoplastic material.

7. The brace of claim 1 wherein the anterior support means is constructed to encompass all of the ankle except an extreme posterior portion of the ankle.

8. A custom fitted brace for limiting eversion and inversion of an ankle and a foot and allowing dorsiflexion and plantar flexion of the ankle and the foot, which comprises:
   a firm anterior support means to be mounted adjacent to and conform to an anterior portion of the ankle, wherein the anterior support means extends only slightly outward away from the ankle over the top of the foot so as to allow dorsiflexion of the foot;
   a firm posterior support means connected to the anterior support means and to be mounted adjacent to and conform to a posterior portion of the ankle, wherein the posterior support means and the anterior support means are secured together by a strap means mounted and secured between the support means and together extend downward beyond the malleoli of the ankle and provide encompassing pressure around the circumference of the ankle and the foot.

9. The brace of claim 8 wherein the strap means is a two sided hook and loop fabric fastener attached to the posterior support means and which is mounted around the anterior support means to secure the anterior and posterior support means together.

10. The brace of claim 8 wherein the anterior support means and the posterior support means are pivotably connected by a quick-release rivet.

11. The brace of claim 8 wherein a cushion means is provided between the anterior portion of the ankle and the anterior support means.

12. The brace of claim 11 wherein the cushion means is constructed of a thermo polyethylene open cell foam.

13. The brace of claim 8 wherein the anterior support means and the posterior support means are constructed of a thermoplastic material.

14. The brace of claim 8 wherein the brace provides pressure around 360° of the ankle and the foot.

15. The brace of claim 8 wherein the brace provides an encompassing pressure around and on the subtalar joint of the ankle to minimize inversion and eversion of the subtalar joint.

16. The brace of claim 1 wherein the posterior support means and the anterior support means are secured together by a strap means mounted and secured between the support means.

17. The brace of claim 16 wherein the strap means is a two sided hook and loop fabric fastener attached to the proximal end of the posterior support means and which is mounted around the anterior support means to secure the anterior and posterior support means together.

18. The brace of claim 8 wherein the distal end of the anterior support means is connected to the distal end of the posterior support means.

19. A custom fitted brace for limiting eversion and inversion of an ankle and a foot which are attached to a leg and allowing dorsiflexion and plantar flexion of the ankle and the foot, which comprises:

(a) a firm anterior support means to be mounted adjacent to and conform to an anterior portion of the ankle, the anterior support means having an arcuate sidewall between a proximal open end and a distal open end along and around a longitudinal axis of the leg wherein the arcuate sidewall at the distal end extends only slightly outward away from the ankle over a top of the foot so as to allow dorsiflexion of the foot; and (b) a firm posterior support means connected to the anterior support means to be mounted adjacent to and conform to a posterior portion of the ankle, the posterior support means having an arcuate sidewall between a proximal open end and a distal open end along and around the longitudinal axis of the leg, wherein the sidewalls define an opening extending between the distal open ends and the proximal open ends and wherein when mounted around the ankle, the anterior support means and the posterior support means together extend downward beyond the malleoli of the ankle and provide encompassing pressure around the circumference of the ankle and the foot.

20. The brace of claim 19 wherein the anterior support means and the posterior support means are able to pivot apart up to about 180°.

21. The brace of claim 19 wherein a posterior opening of the anterior support means is adjacent an extreme posterior portion of the ankle when the brace is mounted around the ankle.

22. The brace of claim 21 wherein an anterior opening of the posterior support means is of a size such as to overlap the sidewall of the anterior support means adjacent the posterior opening of the anterior support means.

23. The brace of claim 19 wherein the distal end of the anterior support means is connected to the distal end of the posterior support means.

24. The brace of claim 22 wherein the posterior support means extends over the anterior support means such that the sidewall of the posterior support means and the sidewall of the anterior support means form a complete enclosure when pivoted together.

25. The brace of claim 19 wherein the distal end of the anterior support means has a pair of tab means extending outward distal and parallel to the longitudinal axis of the leg.

26. The brace of claim 25 wherein the distal end of the posterior support means has a pair of tab means extending outward distal and parallel to the longitudinal axis of the leg.

27. The brace of claim 26 wherein the tab means of the anterior support means is connected to the tab means of the posterior support means.

28. The brace of claim 27 wherein the arcuate sidewall of the anterior support means adjacent the tab means of the anterior support means and the arcuate sidewall of the posterior support means adjacent the tab means of the posterior support means extend over the malleoli of the ankle.

29. The brace of claim 28 wherein the arcuate sidewall adjacent the tab means of the anterior support means and the arcuate sidewall adjacent the tab means of the posterior support means have a convex shape to accommodate the malleoli of the ankle.

30. The brace of claim 21 wherein the proximal open end of the posterior support means extends above the proximal end of the anterior support means when the brace is mounted around the ankle.

31. The brace of claim 19 wherein the anterior support means encompasses all of the ankle except an extreme posterior portion of the ankle.

32. The brace of claim 19 wherein the brace provides 360° pressure around the circumference of the ankle and the foot.

33. The brace of claim 19 wherein the brace provides an encompassing pressure around and on the subtalar joint of the ankle to minimize inversion and eversion of the subtalar joint.

34. A method for limiting inversion and eversion of an ankle and a foot and allowing dorsiflexion and plantar flexion of the ankle and the foot, which comprises:

(a) providing a custom fitted brace for limiting eversion and inversion of an ankle and a foot which comprises: a firm anterior support means having a proximal end and a distal end with an arcuate sidewall therebetween to be mounted adjacent to and conform to an anterior portion of the ankle with the distal end of the anterior support means adjacent the foot and extending only slightly outward away from the ankle over a top of the foot so as to allow dorsiflexion of the foot; and a firm posterior support means having a proximal end and a distal end with an arcuate sidewall therebetween connected to the anterior support means to be mounted adjacent to and conform to a posterior portion of the ankle with the distal end of the posterior support means adjacent the foot, wherein the anterior support means and the posterior support means together extend downward beyond the malleoli of the ankle and provide encompassing pressure around the ankle and the foot;

(b) moving the anterior support means and the posterior support means of the brace apart;

(c) inserting the foot into the brace adjacent the proximal end of the anterior support means and the proximal end of the posterior support means;

(d) positioning the brace over the ankle such that the anterior support means is adjacent the anterior portion of the ankle and the posterior support means is adjacent the posterior portion of the ankle;

(e) moving the anterior support means and the posterior support means together such as to encompass the ankle; and (f) securing the brace around the ankle such that the brace exerts encompassing pressure around the circumference of the ankle and the foot.

35. The method of claim 34 wherein the brace is provided with a strap means adjacent the proximal end of the anterior support means and the proximal end of the posterior support means and the brace is secured around the ankle with the strap means.

36. The method of claim 34 wherein the brace is positioned around the ankle such that the distal end of the anterior support means and the distal end of the posterior support means extend downward adjacent the malleoli of the ankle.

37. The method of claim 34 wherein the distal end of the anterior support means and the distal end of the posterior support means have a convex shape to accommodate the malleoli of the ankle.

* * * * *